(12) United States Patent
Shah et al.

(10) Patent No.: US 10,583,278 B2
(45) Date of Patent: Mar. 10, 2020

(54) APPARATUS, SYSTEM AND METHOD FOR PREVENTING RETENTION OF SURGICAL DRAINS

(71) Applicant: The Trustees of the University of Pennsylvania, Philadelphia, PA (US)

(72) Inventors: Roshan Shah, Chicago, IL (US); Jaimo Ahn, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 534 days.

(21) Appl. No.: 15/104,262

(22) PCT Filed: Dec. 17, 2014

(86) PCT No.: PCT/US2014/070757
§ 371 (c)(1),
(2) Date: Jun. 14, 2016

(87) PCT Pub. No.: WO2015/095281
PCT Pub. Date: Jun. 25, 2015

(65) Prior Publication Data
US 2016/0331945 A1 Nov. 17, 2016

Related U.S. Application Data

(60) Provisional application No. 61/916,885, filed on Dec. 17, 2013.

(51) Int. Cl.
*A61M 27/00* (2006.01)
*A61M 25/01* (2006.01)
*A61M 1/00* (2006.01)

(52) U.S. Cl.
CPC ............ *A61M 27/00* (2013.01); *A61M 1/008* (2013.01); *A61M 25/0102* (2013.01)

(58) Field of Classification Search
CPC .......... A61M 27/00–008; A61M 1/008–0092; A61M 25/0102
See application file for complete search history.

(56) References Cited

U.S. PATENT DOCUMENTS 3,459,189 A 8/1969 Alley et al.
3,528,427 A 9/1970 Sheridan et al.
(Continued)

FOREIGN PATENT DOCUMENTS

WO 2013082671 6/2013

OTHER PUBLICATIONS

International Preliminary Report on Patentability for International Application No. PCT/US2014/070757, dated Jun. 21, 2016, 7 pages.
(Continued)

*Primary Examiner* — Susan S Su
(74) *Attorney, Agent, or Firm* — Baker Botts L.L.P.

(57) ABSTRACT

A surgical drain system includes a drain tube and an obturator configured for insertion in a wound. The obturator can be either solid or hollow, and be positioned inside the drain tube. Alternatively, the obturator can surround the drain tube. The obturator can prevent or limit penetration of a needle through the drain tube as the wound is closed around the drain tube with a suture. In addition, the obturator provides a support that holds the shape of the drain tube during wound closure so that the drain tube is not deformed or crimped by the suture. The obturator can include one or more cutting elements for severing sutures that pierce the drain tube. The one or more cutting elements can also sever or loosen sutures that constrict or otherwise impinge upon the drain tube.

19 Claims, 5 Drawing Sheets

(56) References Cited

U.S. PATENT DOCUMENTS

| | | | |
|---|---|---|---|
| 3,703,899 A | 11/1972 | Calinog | |
| 3,960,153 A * | 6/1976 | Carey | A61M 1/008 |
| | | | 604/164.09 |
| 4,153,058 A * | 5/1979 | Nehme | A61M 25/0606 |
| | | | 604/167.03 |
| 4,508,533 A | 4/1985 | Abramson | |
| 4,810,244 A * | 3/1989 | Allen | A61B 17/3415 |
| | | | 604/164.11 |
| 4,883,474 A * | 11/1989 | Sheridan | A61M 1/008 |
| | | | 604/540 |
| 4,976,684 A | 12/1990 | Broadnax, Jr. | |
| 5,209,736 A | 5/1993 | Stephens et al. | |
| 5,232,440 A | 8/1993 | Wilk | |
| 5,254,120 A | 10/1993 | Cinberg et al. | |
| 5,295,977 A | 3/1994 | Cohen et al. | |
| 5,308,318 A | 5/1994 | Plassche, Jr. | |
| 5,364,365 A * | 11/1994 | Wortrich | A61B 17/3496 |
| | | | 604/158 |
| 5,370,610 A | 12/1994 | Reynolds | |
| 5,489,269 A * | 2/1996 | Aldrich | A61B 17/3415 |
| | | | 604/540 |
| 5,607,405 A | 3/1997 | Decker et al. | |
| 5,628,733 A | 5/1997 | Zinreich et al. | |
| 5,807,317 A | 9/1998 | Krech, Jr. | |
| 5,984,921 A * | 11/1999 | Long | A61B 17/34 |
| | | | 606/48 |
| 6,017,356 A * | 1/2000 | Frederick | A61B 17/3417 |
| | | | 604/264 |
| 6,905,484 B2 | 6/2005 | Buckman et al. | |
| 6,989,003 B2 | 1/2006 | Wing et al. | |
| 7,862,542 B1 | 1/2011 | Harmon, Sr. | |
| 7,905,897 B2 * | 3/2011 | Whitman | A61B 17/3476 |
| | | | 606/172 |
| 2002/0022796 A1 * | 2/2002 | Lawrence | A61M 1/0084 |
| | | | 604/27 |
| 2003/0191497 A1 * | 10/2003 | Cope | A61B 17/0401 |
| | | | 606/215 |
| 2004/0006311 A1 * | 1/2004 | Shchervinsky | A61M 1/008 |
| | | | 604/164.01 |
| 2004/0138531 A1 * | 7/2004 | Bonner | A61B 18/1485 |
| | | | 600/156 |
| 2005/0043682 A1 * | 2/2005 | Kucklick | A61B 17/3421 |
| | | | 604/164.09 |
| 2005/0070821 A1 * | 3/2005 | Deal | A61B 1/018 |
| | | | 600/585 |
| 2005/0261673 A1 * | 11/2005 | Bonner | A61B 18/1485 |
| | | | 606/41 |
| 2006/0217667 A1 * | 9/2006 | Accisano, III | A61M 25/007 |
| | | | 604/174 |
| 2009/0318898 A1 | 12/2009 | Dein | |
| 2011/0270294 A1 * | 11/2011 | Rubin | A61B 17/32002 |
| | | | 606/180 |
| 2012/0253113 A1 * | 10/2012 | Idowu | A61B 1/00094 |
| | | | 600/104 |
| 2015/0330751 A1 * | 11/2015 | Flint | F42B 12/367 |
| | | | 102/507 |
| 2015/0342580 A1 * | 12/2015 | Clancy | A61B 10/04 |
| | | | 600/567 |
| 2017/0245852 A1 * | 8/2017 | Kim | A61B 17/0469 |

OTHER PUBLICATIONS

International Search Report for International Application No. PCT/US2014/070757 dated Mar. 31, 2015.

Written Opinion of the International Searching Authority for International Application No. PCT/US2014/070757 dated Mar. 31, 2015.

* cited by examiner

APPARATUS, SYSTEM AND METHOD FOR PREVENTING RETENTION OF SURGICAL DRAINS

RELATED APPLICATIONS

This application is the U.S. National Phase of International Application No. PCT/US2014/070757, filed Dec. 17, 2014, which is related to and claims the benefit of priority of U.S. Provisional Application Ser. No. 61/916,885, filed Dec. 17, 2013. The contents of International Application No. PCT/US2014/070757 and U.S. Provisional Application Ser. No. 61/916,885 are incorporated by reference herein in their entireties for all purposes.

FIELD

The present disclosure relates to surgical drains generally, and more specifically to apparatuses, systems and methods for preventing the retention of surgical drains in tissue.

BACKGROUND

Surgical drains are used post-surgery to remove fluid (blood, pus, etc.) from wound sites. Unfortunately, surgical drain tubes can become trapped or "retained" inside the wound when the wound is being closed. Drain tube retention can occur when a needle and suture used for wound closure penetrate through the wall of the drain tube. This can result in the drain tube being sewn to the tissue. Drain tube retention can also occur when the suture "lassos" around the drain tube, or where the suture is tightly knotted in such a manner that the suture constricts or impinges upon the drain tube, trapping the drain tube in the wound.

Retained drain tubes can be very difficult or impossible to remove from the wound without breaking the drain tube. When the retained drain tube is pulled forcefully, the drain tube can break, frequently at the location of the sutures, leaving one or more fragments of the tube inside the patient. This can result in the patient having to return to the operating room to have the tube fragment(s) removed. Or, it may be determined that the safest course is to allow the fragment(s) of tube to remain in place, in which case it can, nonetheless, cause a foreign body reaction or be a nidus for infection. Therefore, there is a need for improved apparatuses, systems and methods for inserting surgical drains that reduce or eliminate the occurrence of drain tube retention.

SUMMARY

Drawbacks of conventional apparatuses, systems and methods for inserting surgical drains are addressed by surgical drain systems and methods in accordance with the invention.

In one beneficial aspect of the invention, a surgical drain system can include a drain tube and an obturator configured for insertion in a wound with the drain tube.

In another aspect, the obturator can be an elongated member inserted inside the drain tube.

In another aspect, the obturator can be an elongated member that surrounds at least a portion of the drain tube.

In another aspect, the surgical drain system can include both an elongated member inserted inside the drain tube, and a separate elongated member that surrounds at least a portion of the drain tube.

In another aspect, the obturator can be a solid core elongated member.

In another aspect, the obturator can have a smooth exterior.

In another aspect, the obturator can have one or more cutting elements.

In another aspect, the obturator can include a plurality of serrations.

In another aspect, the obturator can have a longitudinal cutting element.

In another aspect, the obturator can include a linear cutting edge.

In another aspect, the obturator can have one or more cutting elements that extend along the full length of the obturator.

In another aspect, the obturator can have one or more cutting elements that extend along a partial length of the obturator.

In another aspect, the obturator can include a plurality of longitudinal cutting elements.

In another aspect, the obturator can include a plurality of longitudinal cutting elements that are uniformly arranged around a circumference of the obturator.

In another aspect, the obturator can include a roughened section.

In another aspect, the obturator can include one or more cutting elements that wind helically around the obturator.

In another aspect, the obturator can include a sleeve with a distal end, the distal end including one or more cutting elements.

In another aspect, the obturator can include a sleeve with a distal end, the distal end including a plurality of serrations extending around a circumference of the distal end.

In another aspect, the drain tube can include an end cap at an end of the drain tube.

In another aspect, the drain tube can include an end cap that includes a coupling element for coupling to an obturator.

In another aspect, the coupling element includes a bore defined in the end cap.

In another aspect, the obturator can include a removal tool having a coupling end for coupling to an end cap to allow a user to adjust the position of the drain tube or test the closure around the drain tube by manipulating the obturator.

BRIEF DESCRIPTION OF THE DRAWINGS

The foregoing summary and the following description will be better understood in conjunction with the drawing figures, of which.

DETAILED DESCRIPTION

Figure 1:
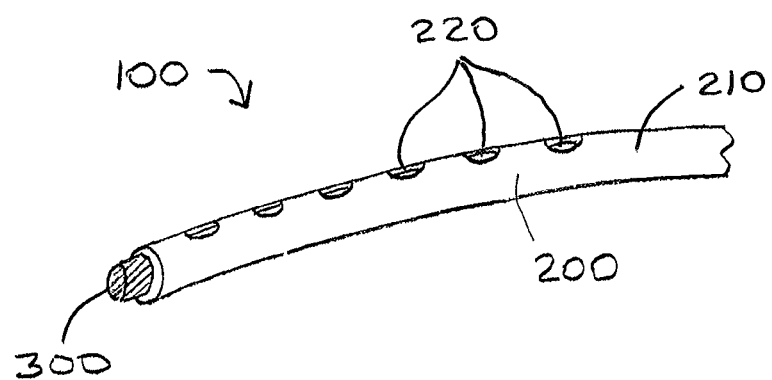
FIG. 1 is a truncated perspective view of a surgical drain system in accordance with one embodiment.
Figure 2:
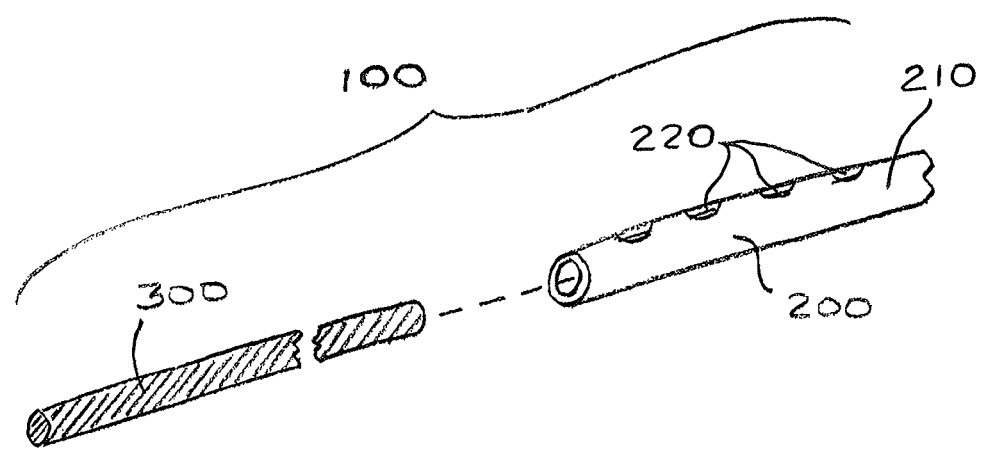
FIG. 2 is an exploded truncated perspective view of the surgical drain system of FIG. 1.

Referring to FIGS. 1 and 2, a surgical drain system 100 is shown in accordance with a first embodiment of the invention. Surgical drain system 100 includes an elongated drain tube 200. Drain tube 200 has a generally cylindrical wall 210. A series of drainage apertures or holes 220 are defined in wall 210. Each hole 220 extends completely through wall 210 to provide open communication between the inside and outside of drain tube 200. Drain tube 200 can be any conventional surgical drain used for the removal of blood, pus and other fluids from a wound, such as a drain manufactured and sold under the federally registered trademark Hemovac®. Surgical drain system 100 also includes a central, closed tubular structure (called an obturator or stylus) 300 that is designed to prevent drain tube 200 from being retained in a wound when the wound is closed.

Drain tubes and obturators in accordance with the invention can have standard lengths, or be cut to a specific length as the situation requires. For purposes of illustration, the drain tubes and obturators are truncated in the attached drawing figures so that they fit within the confines of each drawing sheet.

Obturators in accordance with the invention are configured for insertion in a wound in a generally coaxial relationship with the drain tube. The obturator can be in the form of a hollow obturator that surrounds the drain tube, or a hollow or solid obturator that is inserted inside the drain tube. In surgical drain system 100, which is just one example, obturator 300 is a solid core elongated member that is inserted inside drain tube 200, or comes pre-inserted into drain tube 200, so that the obturator and drain tube extend in a coaxial relationship. Obturator 300 may be formed of any flexible material that is suitable for use in wound closure, yet sufficiently rigid to resist or prevent penetration from a needle and suture, as well as prevent or limit deformation or crimping of the drain tube by the suture during closure of the wound. For example, obturator 300 may be formed of high density polyethylene or polypropylene. Once in place, obturator 300 forms a rigid support column inside drain tube 200 that prevents the drain tube from being retained inside the wound by sutures that penetrate the drain tube. The solid core of the obturator makes it difficult for a needle to pass through drain tube 200, or stops a needle shortly after it penetrates or partially penetrates the drain tube. The solid core also gives feedback to the surgeon to pass a different suture. Obturator 300 also forms a rigid support to hold the shape of the drain tube 200 so that the drain tube is not crimped or otherwise impinged upon by sutures that are passed around the tube, thereby preventing the drain tube from being constricted and retained inside the wound. The exterior of obturator 300 is generally smooth. It will be understood, however, that obturators in accordance with the invention can have various surface textures, including surfaces with roughened areas, ridges or other protuberances. Obturator 300 is easily withdrawn from the drain tube 200 after wound closure.

Surgical drain system 100 can be utilized in the following manner to establish a drain in a wound. In one embodiment, surgical drain system 100 arrives to the surgeon with drain tube 200 and obturator 300 preassembled. In another embodiment, drain tube 200 and obturator 300 arrive as separate parts that are assembled by the end user prior to use. In the latter case, obturator 300 is attached to drain tube 200 by inserting the obturator into the interior of the drain tube. The outer diameter of obturator 300 is slightly less than the inner diameter of drain tube 200 to allow the obturator to advance easily into the drain tube, but not so much less as to allow passage of a needle or suture through the drain tube.

With obturator 300 positioned in drain tube 200, the obturator and drain tube are inserted into a wound. The wound is then sutured to close the wound with care to avoid incorporating obturator 300 and drain tube 200 into the closure. As the wound is being closed, any needles that contact drain tube 200 will be met with resistance from the rigid obturator 300, greatly reducing the risk of the tube being sewn into the wound. Obturator 300 will also prevent drain tube 200 from cinching, collapsing, buckling or otherwise deforming in response to suturing during wound closure. Once the wound is closed around surgical drain system 100, obturator 300 is removed from drain tube 200 while leaving the drain tube in the wound closure.

Once a drain tube and obturator in accordance with the invention are inserted and the wound is closed, the drain tube and obturator can be pulled to see if the drain tube is retained, as in the case of a drain tube impinged by a suture. This might be checked immediately after the wound is closed. In the event that the drain tube is retained, the suture(s) holding the drain tube can be easily severed to release the drain tube using a number of alternative obturator designs in accordance with the invention. Also, because of the rigidity of the obturator, the drain tube alone can be pulled relative to the wound while the obturator remains in place, to test whether or not the drain tube is retained or trapped in the wound. Once it is confirmed the drain tube is free (i.e. not retained or trapped in the wound by a suture, for example), the drain tube can be pushed back into its original and desired position over the obturator.

Figure 3:
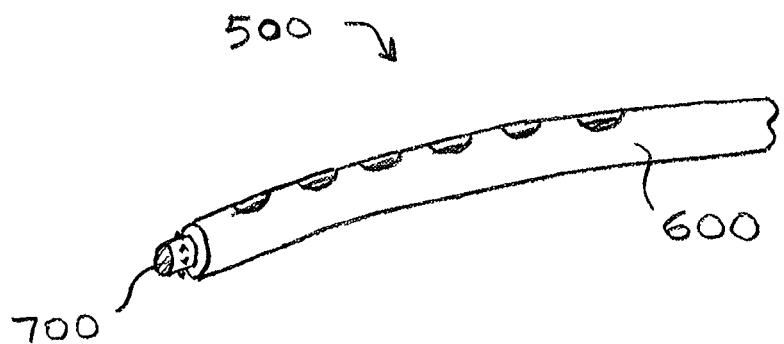
FIG. 3 is a truncated perspective view of a surgical drain system in accordance with another embodiment.
Figure 4:
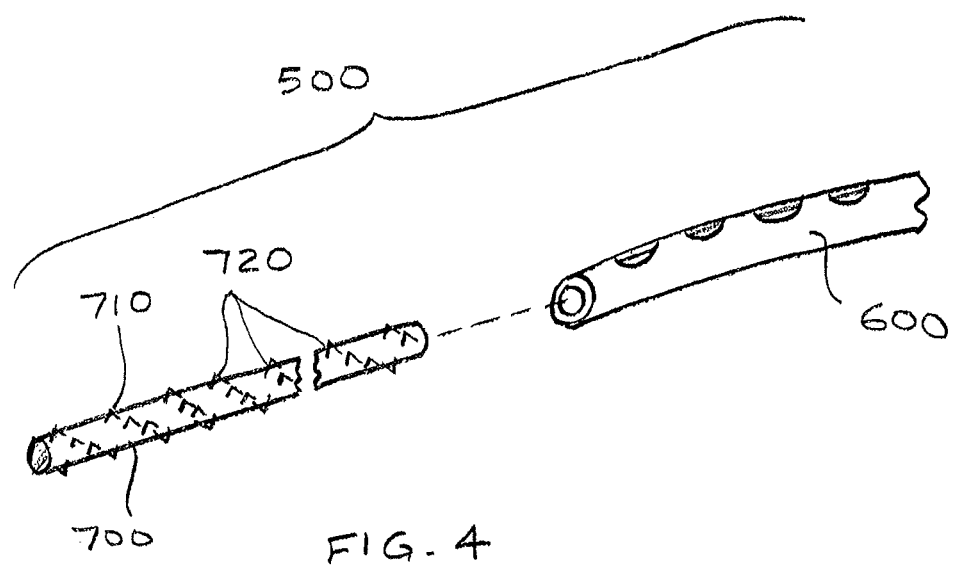
FIG. 4 is an exploded truncated perspective view of the surgical drain system of FIG. 3.

FIGS. 3 and 4 show an alternative surgical drain system 500. Surgical drain system 500 includes a drain tube 600 (which can be identical to drain tube 200 in the first embodiment) and an obturator 700 with an external cutting edge 710. Cutting edge 710 has a number of serrations 720 that are configured to sever any sutures that pierce drain tube 600, particularly if the suture path is between the obturator and drain tube, when the wound is closed around surgical drain system 500. Serrations 720 are also configured to sever or loosen any sutures that constrict or otherwise impinge upon and hold the drain tube in the wound. Any sutures that hold the drain tube 600 can be severed by axially rotating or "spinning" obturator 700 relative to the drain tube 600, which is held stable. As obturator 700 is rotated, serrations 720 can rotate or oscillate in a sawing motion to sever sutures that retain drain tube 600. Like obturator 300, obturator 700 forms a rigid support column inside drain tube 600 that holds the shape of the drain tube and prevents the drain tube from being sewn or constricted inside the wound.

Figure 5:
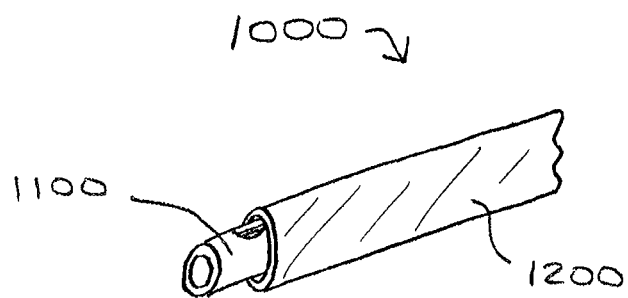
FIG. 5 is a truncated perspective view of a surgical drain system in accordance with another embodiment.
Figure 6:
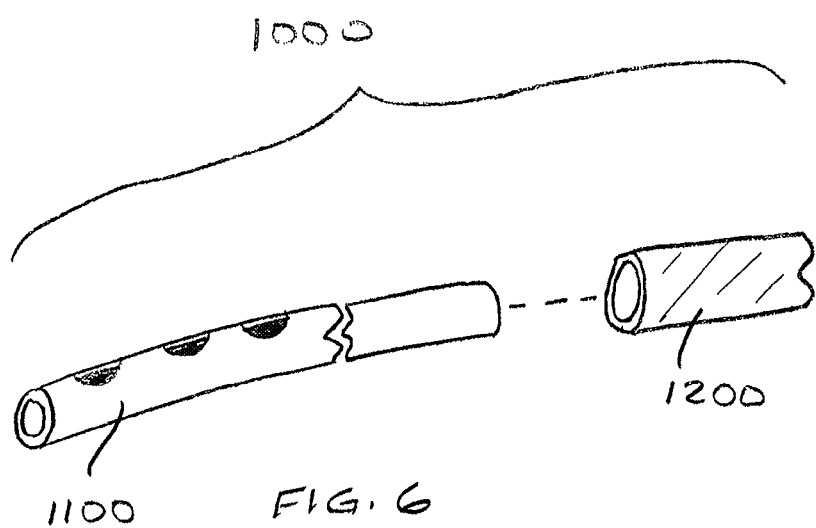
FIG. 6 is an exploded truncated perspective view of the surgical drain system of FIG. 5.

FIGS. 5 and 6 show another surgical drain system 1000 in accordance with the invention. Unlike the previous embodiments, surgical drain system 1000 features a drain tube 1100 that is protected by an obturator 1200 on the outside of the drain tube. Obturator 1200 acts as a shield or sleeve that protects drain tube 1100 from being pierced by a needle and suture. Obturator 1200 also provides a barrier around drain tube 1100 that prevents the wound from being closed so tightly that the tissue and/or sutures impinge on the drain tube, thereby reducing the risk of the drain tube being retained in the wound closure.

By using surgical drain systems in accordance with the invention, medical professionals and hospitals can reduce the occurrence of surgical drain retention and the associated complications.

Figure 7:
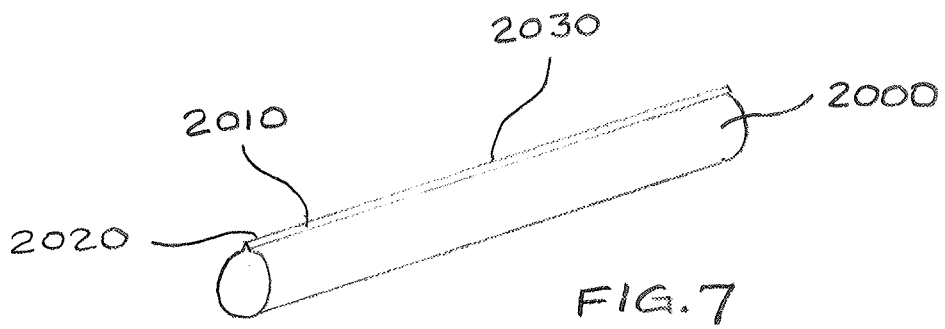
FIG. 7 is a truncated perspective view of an obturator component in accordance with another embodiment.

Obturators in accordance with the invention can have one or more cutting elements for severing sutures. Serrations, such as serrations 720 shown in FIGS. 3 and 4, are just one example. The number, type, sharpness and physical arrangement of cutting elements can be selected based on multiple factors, including the type of suture being used. FIGS. 7-10 show additional examples of cutting elements in accordance with the invention. FIG. 7 shows an obturator 2000 with a longitudinal cutting element 2010 extending along the length of the obturator. Longitudinal cutting element 2010 has a V-shaped cross section that forms an apex or point 2020. Point 2020, which can be blunt or sharp, forms a linear cutting edge 2030 extending along the length of obturator 2000. Linear cutting edge 2030 can be used to sever sutures that impinge or penetrate a drain tube. Although longitudinal cutting element 2010 is shown extending along the full length of obturator 2000, cutting elements in accordance with the invention need not extend the full length of the obturator. In many instances, only a small fraction of the length of the obturator is used to sever sutures. As such, cutting elements in accordance with the invention can extend along only a small section of an obturator, or along multiple small sections that are separated from one another by sections without cutting elements.

Only one longitudinal cutting element 2010 is shown in FIG. 7. Obturators in accordance with the invention can also feature two, three, four or more longitudinal cutting elements identical to cutting element 2010. Longitudinal cutting elements like cutting element 2010 can be arranged uniformly around the circumference of the obturator, with each cutting element offset from adjacent cutting elements by a uniform angle. Alternatively, longitudinal cutting elements can be arranged non-uniformly around the circumference of the obturator, so that each cutting element is separated from an adjacent cutting element by a unique angle that varies from one pair of cutting elements to the next.

Figure 8:
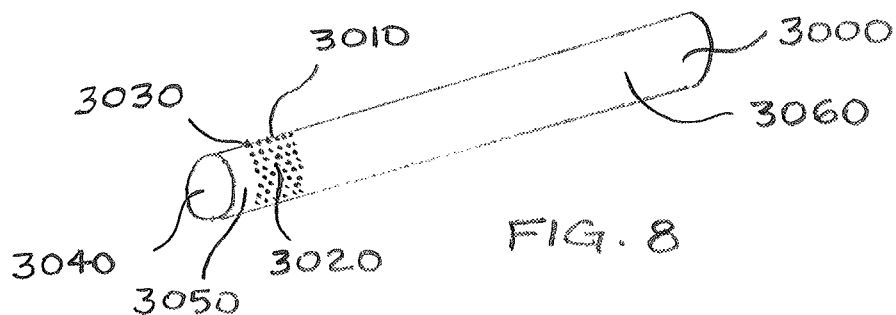
FIG. 8 is a truncated perspective view of an obturator component in accordance with another embodiment.

FIG. 8 shows an obturator 3000 with another cutting element 3010 in accordance with the invention. Cutting element 3010 includes a coarse or roughened section 3020 made up of small projections 3030. Roughened section 3020 extends along a short segment of obturator 3000 that is offset from an end 3040 of the obturator. A short smooth section 3050 without projections is defined between roughened section 3020 and end 3040. A long smooth section 3060 extends on the opposite side of roughened section 3020. Long smooth section 3060 can be used to hold obturator 3000 during insertion or severing of sutures.

Figure 9:
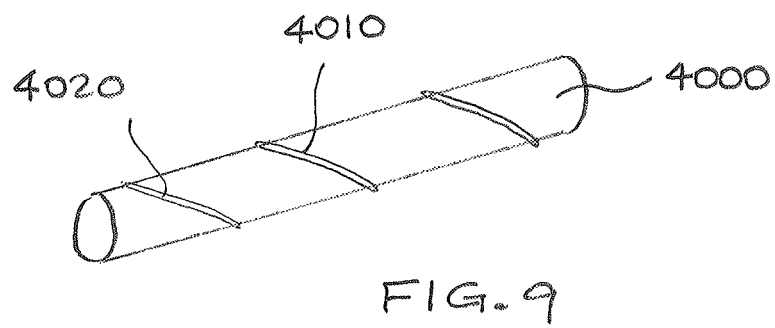
FIG. 9 is a truncated perspective view of an obturator component in accordance with another embodiment.

FIG. 9 shows an obturator 4000 with another cutting element 4010 in accordance with the invention. Cutting element 4010 includes a V-shaped projection 4020, similar to cutting element 2010, that extends or winds helically around the circumference of obturator 4000.

Figure 10:
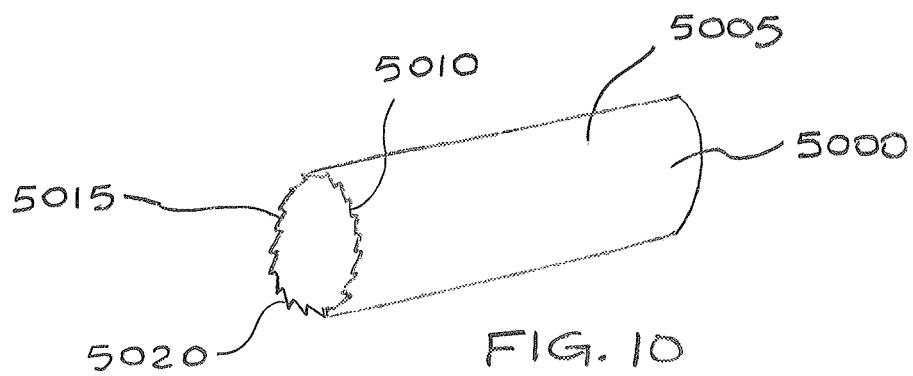
FIG. 10 is a truncated perspective view of an obturator component in accordance with another embodiment.

FIG. 10 shows an obturator 5000 with another cutting element 5010 in accordance with the invention. Obturator 5000 includes a hollow sleeve 5005 that can be placed over or around a drain tube, with the drain tube inserted inside the obturator. Sleeve 5005 has a distal edge 5015 with cutting element 5010 extending around the circumference of the edge. Cutting element 5010 includes a plurality of serrations 5020. To sever sutures, distal edge 5015 and serrations 5020 are placed in contact with the sutures, and sleeve 5005 is rotated or twisted.

Surgical drain systems in accordance with the invention can optionally be provided with one or more mechanisms to aid in securing the obturator into the drain tube until the obturator is ready for removal. This would facilitate the unitary movement of the drain tube and obturator when checking whether the drain tube is retained, or when advancing the drain tube if it is partially pulled out. For example, surgical drain systems in accordance with the invention can include an end cap that is constructed at the terminal end of the drain tube, and which can be detachably connected with an end of the obturator by a threaded connection or other detachable coupling. In such a configuration, the drain tube can be inserted into the patient with the obturator and end cap. Once the drain tube is properly positioned, the obturator can be detached from the end cap by rotating and unscrewing, or otherwise de-coupling, the obturator from the end cap. The obturator can then be freely removed.

Another example of an end cap in accordance with the invention includes an end cap and obturator or other implement that can be inserted and placed into the drain tube that is already in place within the patient. This form of end cap and obturator may include an end cap that is inserted in a radially collapsed condition to the deepest end of the drain tube, or an intermediate location in the drain tube. Once the end cap is positioned in the desired location, the end cap can be radially expanded to engage the wall of the drain tube. Once engaged with the drain tube wall, the end cap and obturator can withdraw the captured drain tube. The implement used for pulling the end cap can either be permanently connected or detachably connected to the end cap.

Figure 11:
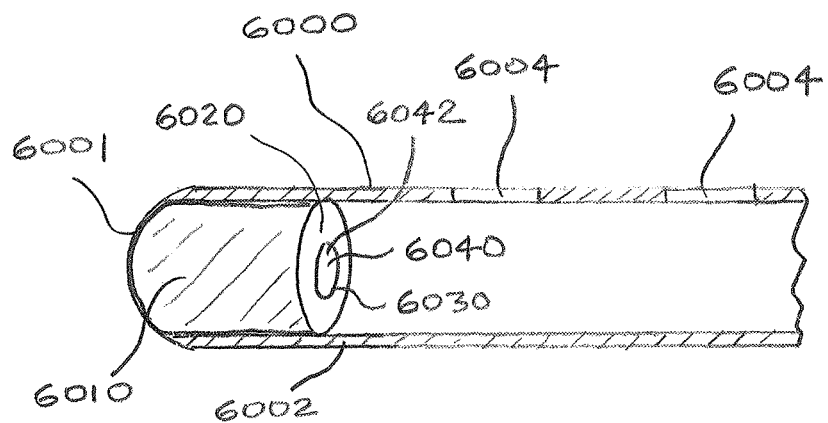
FIG. 11 is a truncated perspective view of a drain tube shown in cross section in accordance with another embodiment.

Referring to FIG. 11, one example of a drain tube 6000 is shown with an end cap 6010 in more detail. Drain tube 6000 includes a cylindrical tube wall 6002 and drainage holes 6004 extending through the tube wall. End cap 6010 is fixed inside an end 6001 of drain tube 6000. End caps in accordance with the invention can be fixed to drain tubes in a number of ways, including a press fit, adhesive bond, or other suitable connection.

End cap 6010 has a coupling end 6020 that faces inside tube 6000. When drain tube 6000 is secured in a patient, the drain tube can be removed from the patient or otherwise adjusted without risk of breaking the tube by attaching an obturator to end cap 6010. Coupling end 6020 has a coupling element 6030 in the form of a bore 6040. Bore 6040 is adapted to receive a coupling end of an obturator, to attach the obturator to the end cap. The obturator can be a simple cylindrical shaft with a coupling end, or a specially designed removal tool.

Figure 12:
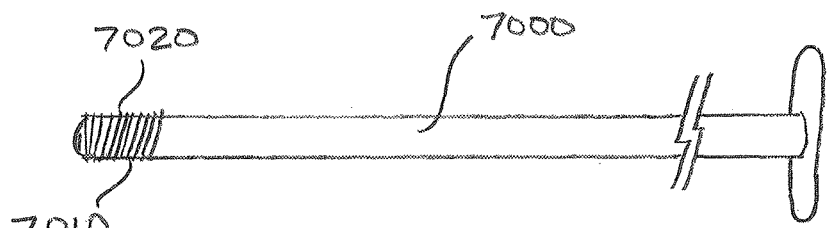
FIG. 12 is a truncated perspective view of a removal instrument in accordance with one embodiment.

In one possible embodiment, the inside wall 6042 of bore 6040 includes a female thread that can be threadingly engaged with a male thread 7020 on a coupling end 7010 of a threaded obturator 7000, which is shown in FIG. 12. Obturator 7000 can be inserted into drain tube 6000 until coupling end 7010 begins to enter bore 6040, at which point the coupling end is rotated to screw the coupling end into the bore. To improve engagement, coupling end 7010 can be formed of a magnetic material that is attracted to end cap 6000.

Figure 13:
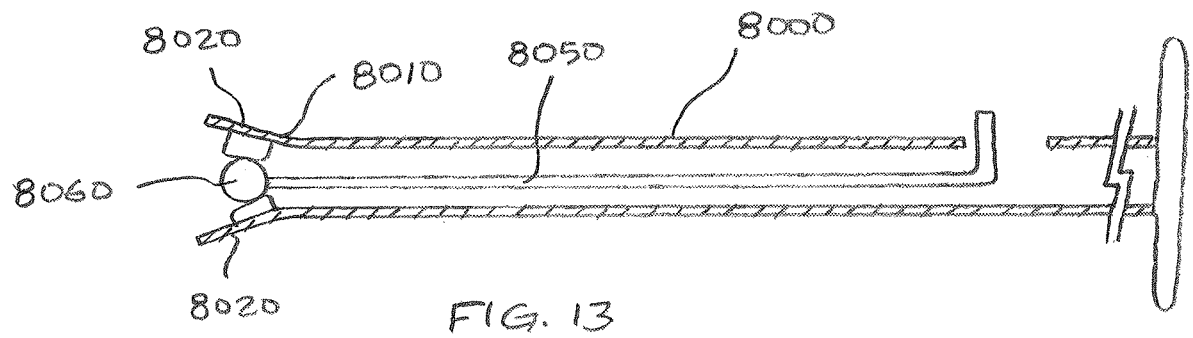
FIG. 13 is a truncated perspective view of a removal instrument in accordance with another embodiment.

In another possible embodiment, the bore 6040 has a generally smooth wall adapted to engage an expandable obturator 8000, which is shown in FIG. 13. Obturator 8000 has a coupling end 8010 comprising a plurality of gripping elements or fingers 8020. Gripping elements 8020 can be expanded or splayed radially outwardly to engage inner wall 6042 of bore 6040, creating a compressed or frictional engagement. Gripping elements 8020 can be expanded by advancing an internal expansion element 8050 in a distal direction inside obturator 8000, until an engagement end 8060 contacts the gripping elements and pushes them outwardly. Coupling end 8010 and gripping elements 8020 are formed of resilient flexible material. When expansion element 8050 is moved in a proximal direction to move engagement end 8060 out of contact with gripping elements 8020, stored energy in the resilient gripping elements causes the gripping elements to move radially inwardly and return to their original positions, allowing the gripping elements to be removed from bore 6040.

While preferred embodiments of the invention have been shown and described herein in the form of specific embodiments, it will be understood that such embodiments are provided by way of example only. Numerous variations, changes and substitutions will occur to those skilled in the art without departing from the scope of the invention.

In addition, the present invention contemplates any combination of features shown in the different embodiments described herein. For example, the present invention contemplates examples of surgical drain systems having protective sleeves on the outside of the drain tube, where the sleeves have cutting edges along at least a portion of the sleeve's exterior, in the interior of the sleeve, or both the exterior and interior. Apparatuses, systems and methods of the present invention can be used when closing open wounds caused by injury or by open surgery. Accordingly, it is intended that the appended claims cover all such variations as fall within the scope of the invention.

What is claimed:

1. A surgical drain system comprising:
a drain tube; and
the obturator configured for insertion in a wound in a generally coaxial relationship with the drain tube, the obturator separately removable from the wound, and including at least one cutting element having a plurality of serrations extending continuously around a perimeter of the obturator and configured to sever sutures penetrating or impinging on the drain tube.

2. The surgical drain system of claim 1, wherein the obturator is an elongated member inserted inside the drain tube.

3. The surgical drain system of claim 1, wherein the obturator is an elongated member that surrounds at least a portion of the drain tube.

4. The surgical drain system of claim 1, wherein the obturator has a smooth exterior.

5. The surgical drain system of claim 1, wherein the cutting element comprises a longitudinal cutting element.

6. The surgical drain system of claim 1, wherein the cutting element comprises a linear cutting edge.

7. The surgical drain system of claim 1, wherein the cutting element extends along the full length of the obturator.

8. The surgical drain system of claim 1, wherein the cutting element extends along a partial length of the obturator.

9. The surgical drain system of claim 1, wherein the cutting element comprises a plurality of longitudinal cutting elements.

10. The surgical drain system of claim 9, wherein the plurality of longitudinal cutting elements are uniformly arranged around a circumference of the obturator.

11. The surgical drain system of claim 1, wherein the cutting element comprises a roughened section.

12. The surgical drain system of claim 1, wherein the cutting element winds helically around the obturator.

13. The surgical drain system of claim 1, wherein the obturator comprises a sleeve with a distal end, the distal end comprising the cutting element.

14. The surgical drain system of claim 13, wherein the plurality of serrations extend around a circumference of the distal end of the sleeve.

15. The surgical drain system of claim 1, further comprising an end cap at an end of the drain tube.

16. The surgical drain system of claim 15, wherein the end cap comprises a coupling element for coupling to the obturator.

17. The surgical drain system of claim 16, wherein the coupling element comprises a bore defined in the end cap.

18. The surgical drain system of claim 1, wherein the obturator is a solid core elongated member.

19. A surgical drain system comprising:
a drain tube;
an end cap at an end of the drain tube; and
an obturator including at least one cutting element configured to sever sutures, wherein the end cap comprises coupling element including a bore defined in the end cap for coupling to the obturator, the obturator configured for insertion in a wound in a generally coaxial relationship with the drain tube and including a removal tool having a coupling end for coupling to the end cap to allow a user to adjust the position of the drain tube or test the closure around the drain tube by manipulating the obturator.

* * * * *